(12) United States Patent
Sugaya

(10) Patent No.: US 10,690,644 B2
(45) Date of Patent: Jun. 23, 2020

(54) COMPUTER SYSTEM, PLANT DIAGNOSIS METHOD, AND PROGRAM

(71) Applicant: OPTIM CORPORATION, Saga (JP)

(72) Inventor: Shunji Sugaya, Tokyo (JP)

(73) Assignee: OPTIM CORPORATION, Saga (JP)

( * ) Notice: Subject to any disclaimer, the term of this patent is extended or adjusted under 35 U.S.C. 154(b) by 0 days.

(21) Appl. No.: 16/492,416

(22) PCT Filed: Oct. 18, 2016

(86) PCT No.: PCT/JP2016/080871
§ 371 (c)(1),
(2) Date: Sep. 9, 2019

(87) PCT Pub. No.: WO2018/073899
PCT Pub. Date: Apr. 26, 2018

(65) Prior Publication Data
US 2020/0041475 A1 Feb. 6, 2020

(51) Int. Cl.
*G06K 9/00* (2006.01)
*G01N 33/00* (2006.01)
(Continued)

(52) U.S. Cl.
CPC ........... *G01N 33/0098* (2013.01); *A01G 7/00* (2013.01); *G01N 21/3563* (2013.01);
(Continued)

(58) Field of Classification Search
CPC ........... G06T 2207/10048; G06T 2207/30188; G01N 33/0098; G06K 2209/17; G06K 9/00657

See application file for complete search history.

(56) References Cited

U.S. PATENT DOCUMENTS

| | | | | |
|---|---|---|---|---|
| 5,133,605 A | * | 7/1992 | Nakamura | G08B 13/194 250/330 |
| 2015/0254860 A1 | * | 9/2015 | Wang | G06K 9/6227 382/190 |

(Continued)

FOREIGN PATENT DOCUMENTS

| | | | | |
|---|---|---|---|---|
| CN | 200996939 | * | 12/2007 | G01N 21/27 |
| CN | 106067169 | * | 11/2016 | G01N 21/27 |

(Continued)

OTHER PUBLICATIONS

SeA, Raza, et al. "Automatic Detection of Diseased Tomato Plants Using Thermal and Stereo Visible Light Images." PLoS ONE 10.4 (2015): e0123262. (Year: 2015).*

(Continued)

*Primary Examiner* — Li Liu
(74) *Attorney, Agent, or Firm* — Norton Rose Fulbright US LLP; James R. Crawford

(57) ABSTRACT

The purpose of the present disclosure is to provide a computer system, a plant diagnosis method, and a program in which the measurement accuracy of the temperature of each site of a target is improved. The computer system acquires a visible light image and an infrared image that are imaged by a camera, identifies a region, in the visible light image, which corresponds to a predetermined site of a plant imaged by the camera, identifies a region, in the infrared image, which corresponds to the identified region in the visible light image, and diagnoses the plant based on the temperature of the identified region in the infrared image.

9 Claims, 10 Drawing Sheets

(51) Int. Cl.
*G06T 7/10* (2017.01)
*G06T 7/90* (2017.01)
*A01G 7/00* (2006.01)
*G01N 21/3563* (2014.01)
*G06T 7/00* (2017.01)

(52) U.S. Cl.
CPC .............. *G06T 7/0012* (2013.01); *G06T 7/10* (2017.01); *G06T 7/90* (2017.01); *G06T 2207/10024* (2013.01); *G06T 2207/10048* (2013.01)

(56) References Cited

U.S. PATENT DOCUMENTS

| | | | | |
|---|---|---|---|---|
| 2015/0302241 | A1* | 10/2015 | Eineren | A01J 5/007 382/110 |
| 2016/0216245 | A1* | 7/2016 | Sutton | G01N 33/0098 |
| 2017/0286772 | A1* | 10/2017 | Workman | A01G 22/00 |
| 2018/0082412 | A1* | 3/2018 | Greenberg | G06K 9/00657 |
| 2018/0180768 | A1* | 6/2018 | Wolf | G01W 1/02 |
| 2018/0350053 | A1* | 12/2018 | Sugaya | G06T 7/001 |
| 2019/0079011 | A1* | 3/2019 | Frangioni | G01N 21/6428 |
| 2019/0159681 | A1* | 5/2019 | Sugaya | G06T 7/70 |

FOREIGN PATENT DOCUMENTS

| | | |
|---|---|---|
| JP | H11120458 A | 4/1999 |
| JP | 2002022652 A | 1/2002 |
| JP | 2002132341 A | 5/2002 |
| JP | 2003310055 A | 11/2003 |

OTHER PUBLICATIONS

Sanchez, Victor, et al. "Registration of thermal and visible light images of diseased plants using silhouette extraction in the wavelet domain." Pattern Recognition 48.7 (2015): 2119-2128. (Year: 2015).*

Barbedo, Jayme Garcia Arnal. "A review on the main challenges in automatic plant disease identification based on visible range images." Biosystems engineering 144 (2016): 52-60. (Year: 2016).*

Belin, Étienne, et al. "Thermography versus chlorophyll fluorescence imaging for detection and quantification of apple scab." Computers and electronics in agriculture 90 (2013): 159-163. (Year: 2013).*

Han, Ju, and Bir Bhanu. "Fusion of color and infrared video for moving human detection." Pattern Recognition 40.6 (2007): 1771-1784. (Year: 2007).*

Bridgestone Corp. News Release: "Established disease diagnosis technology for natural rubber resource "para rubber tree"", Jul. 10, 2012, Googletranslate from http://www.bridgestone.co.jp/corporate/news/2012071001.html.

International Search Report issued in PCT/JP2016/080871 dated Jan. 24, 2017.

* cited by examiner

Reference Temperature Database

| Site | Reference temperature (°C) |
|---|---|
| Stem | 18 |
| Branch | 17 |
| Leaf | 20 |

Fig. 10

COMPUTER SYSTEM, PLANT DIAGNOSIS METHOD, AND PROGRAM

This application is a 371 of International Patent Application No. PCT/JP2016/080871 filed on Oct. 18, 2016, which is incorporated herein by reference in its entirety.

TECHNICAL FIELD

The present disclosure relates to a computer system, a plant diagnosis method and program that image and diagnosis a plant.

BACKGROUND ART

In recent years, a computer system capable of diagnosing disease of a plant by imaging an image of the plant is proposed.

In such a computer system, a configuration in which a disease diagnosis is performed by measuring a change in temperature or color of the plant using a spectrometer or an infrared thermography is disclosed (see Non Patent Document 1).

CITATION LIST

Non-Patent Document

Non-Patent Document 1: http://www.bridgestone.co.jp/corporate/news/2012071001.html

SUMMARY

Technical Problem

However, in the configuration of Non Patent Document 1, there is a temperature difference for each site of the plant, and in order to accurately grasp the disease state, it is necessary to accurately measure the temperature of each site of a target whose temperature is to be measured. However, although a contour or an approximate site of the plant can be identified from a thermographic image, the exact position of each site is difficult to be identified due to the distance from the camera to the imaged target or other factors. As a result, there is a limit in improving the accuracy of the temperature measured for each site.

The purpose of the present disclosure is to provide a computer system, a plant diagnosis method, and a program in which the measurement accuracy of the temperature of each site of the target is improved.

Solution to Problem

The present disclosure provides the following solutions.

The present disclosure provides a computer system including a first acquisition unit configured to acquire a visible light image and an infrared image that are imaged by a camera, a first image processing unit configured to identify a region, in the visible light image, which corresponds to a predetermined site of a plant imaged by the camera, a second image processing unit configured to identify a region, in the infrared image, which corresponds to the identified region in the visible light image, and a diagnosis unit configured to diagnosis the plant based on the temperature of the identified region in the infrared image.

According to the present disclosure, the computer system acquires the visible light image and the infrared image imaged by the camera, identifies the region, in the visible light image, which corresponds to the predetermined site of the plant imaged by the camera, identifies the region, in the infrared image, which corresponds to the identified region in the visible light image, and diagnoses the plant based on the temperature of the identified region in the infrared image.

The present disclosure is a category of computer system, and exerts the same function/effect according to the category even in other categories such as a plant diagnosis method and program.

Advantageous Effects of Invention

According to the present disclosure, it is capable of providing a computer system, a plant diagnosis method, and a program in which the measurement accuracy of the temperature of each site of the target is improved.

BRIEF DESCRIPTION OF DRAWINGS

FIG. 10 is a diagram illustrating an example of a reference temperature database stored in the computer 10.

DESCRIPTION OF EMBODIMENTS

Hereinafter, the best aspect for carrying out the present disclosure will be described with reference to the drawings. Note that, this is merely an example, and the technical scope of the present disclosure is not limited to this.

Outline of Plant Diagnosis System 1

Figure 1:
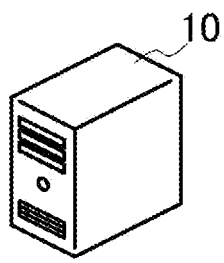
FIG. 1 is a diagram illustrating an outline of a plant diagnosis system 1.
Figure 1:
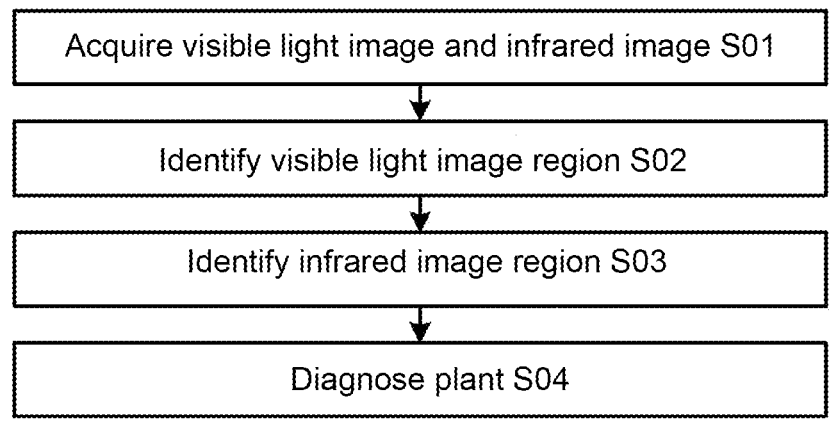

Based on FIG. 1, an outline of the present disclosure will be described. FIG. 1 is a diagram for explaining the outline of a plant diagnosis system 1 according to a suitable embodiment of the present disclosure. The plant diagnosis system 1 includes a computer 10, acquires an image obtained by imaging a plant, and diagnoses the plant.

The computer 10 is a computing device communicably connected to a visible light camera, an infrared camera, a sensor, an environmental adjustment device, and the like (not illustrated). The plant diagnosis system 1 acquires a visible light image from the visible light camera, acquires an infrared image from the infrared camera, acquires environmental information about living environment of the plant such as brightness, wind direction, wind speed, temperature, ambient temperature, humidity, atmospheric pressure from the sensor, and transmits instruction for adjusting the living environment to an environment adjustment device such as a lighting device (various lights, etc.), an air-conditioner (blower, etc.), and a water sprinkler.

First, the computer 10 acquires a visible light image and an infrared image imaged by a camera that is not illustrated (step S01). The computer 10 acquires the visible light image such as a moving image, a still image of the plant imaged by the visible light camera. Further, the computer 10 acquires the infrared image such as a moving image, a still image of the plant imaged by the infrared camera. The visible light camera and the infrared camera are disposed side by side or in the vicinity, and the visible light camera and the infrared camera image the same target. That is, the visible light camera and the infrared camera image the same target from substantially the same imaging point.

The computer 10 identifies, in the visible light image, a visible light image region which is a region corresponding to a predetermined site of the plant imaged by a camera (step S02). The computer 10 identifies, for example, a part of a structure such as a flower, a branch, a leaf, a preset site as the predetermined site of the plant, or the like. For example, the computer 10 identifies a region, in the visible light image, which corresponds to the predetermined site by performing image analysis. The computer 10 extracts a feature value present in the visible light image, and identifies the predetermined site based on the feature value. Further, the computer 10 extracts a color of the visible light image, and identifies the predetermined site based on the color.

The computer 10 identifies, in the infrared image, an infrared image region that is a region in the infrared image corresponding to the region in the visible light image described above (step S03). The computer 10 identifies a region in the infrared image coincident with the visible light image region as the infrared image region by comparing the visible light image and the infrared image. The computer 10 identifies a region of the infrared image located at the same position as the position of the visible light image as the infrared image region.

The computer 10 diagnoses the plant based on the temperature of the infrared image region (step S04). The computer 10 diagnoses whether a disease occurs in the plant, for example, by comparing the temperature of the infrared image region with the temperature when a disease occurs in the plant.

The above is the outline of the plant diagnosis system 1.

System Configuration of Plant Diagnosis System 1

Figure 2:
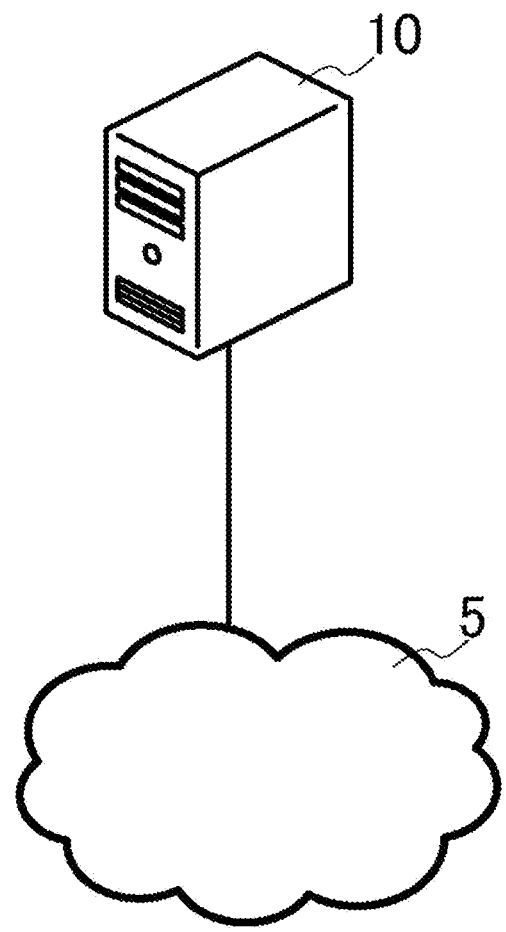
FIG. 2 is an overall configuration diagram of the plant diagnosis system 1.

Based on FIG. 2, a system configuration of the plant diagnosis system 1 will be described. FIG. 2 is a diagram illustrating the system configuration of the plant diagnosis system 1 according to a suitable embodiment of the present disclosure. The plant diagnosis system 1 includes a computer 10 and a public network (the Internet, the third and fourth generation communication networks, etc.) 5, acquires an image obtained by imaging a plant, and diagnoses the plant.

The plant diagnosis system 1 is connected to cameras such as a visible light camera configured to image the visible light image of the plants and an infrared camera configured to image the infrared image of the plants, various sensors configured to detect the environmental information indicating the living environment of the plant such as brightness, wind direction, wind speed, temperature, ambient temperature, humidity, atmospheric pressure, and the environment adjustment device configured to adjust the living environment of the plant, such as an air-conditioner, a water sprinkler, a medicine sprayer. The computer 10 acquires various kinds of information from these devices and transmits various instructions.

The computer 10 is the above-described computing device having functions to be described later.

Description of Each Function

Figure 3:
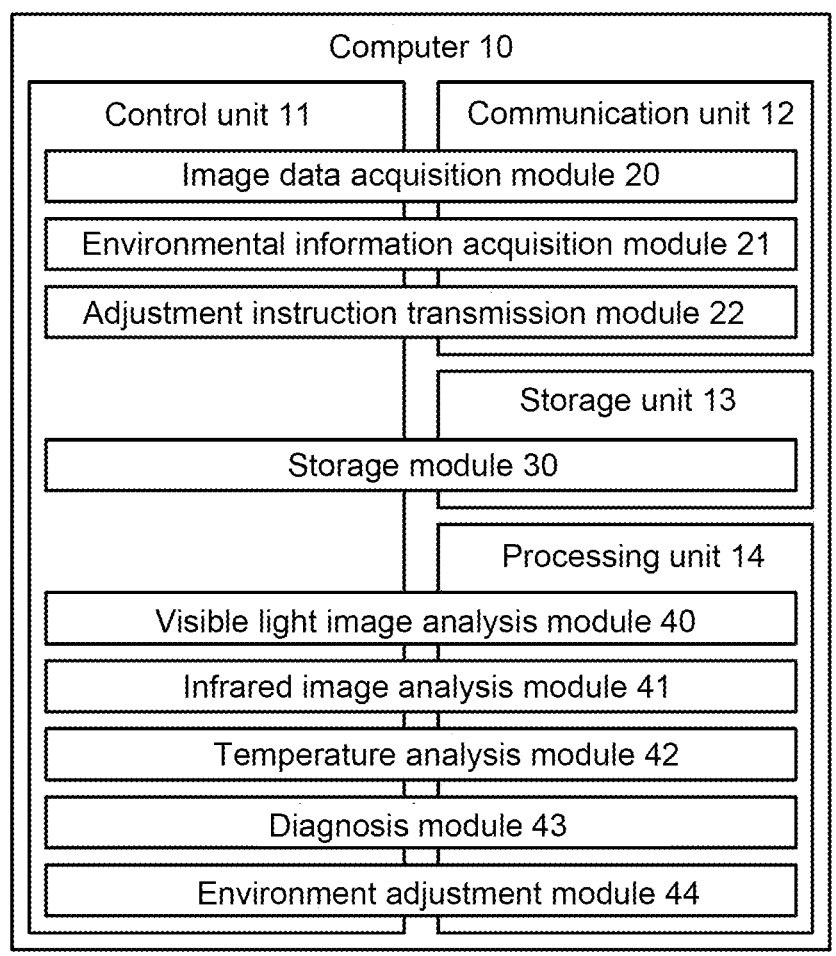
FIG. 3 is a functional block diagram of a computer 10.

Based on FIG. 3, the functions of the plant diagnosis system 1 will be described. FIG. 3 is a functional block diagram of the computer 10.

The computer 10 includes a central processing unit (CPU), a random access memory (RAM), a read only memory (ROM), and the like as a control unit 11, and a device enabling communication with other devices (cameras, various sensors, environment adjustment devices, etc.) as a communication unit 12, for example, a WiFi (Wireless Fidelity) compliant device construed under IEEE802.11. Further, the computer 10 includes a data storage unit such as a hard disk, a semiconductor memory, a recording medium, a memory card as a storage unit 13. Further, the computer 10 includes a device and the like configured to execute various processes such as image processing and disease diagnosis as a processing unit 14.

In the computer 10, the control unit 11 reads a predetermined program in cooperation with the communication unit 12 to realize an image data acquisition module 20, an environmental information acquisition module 21, and an adjustment instruction transmission module 22. Further, in the computer 10, the control unit 11 reads a predetermined program in cooperation with the storage unit 13 to realize a storage module 30. Further, in the computer 10, the control unit 11 reads a predetermined program in cooperation with the processing unit 14 to realize a visible light image analysis module 40, an infrared image analysis module 41, a temperature analysis module 42, a diagnosis module 43, and an environment adjustment module 44.

Plant Diagnosis Process

Figure 4:
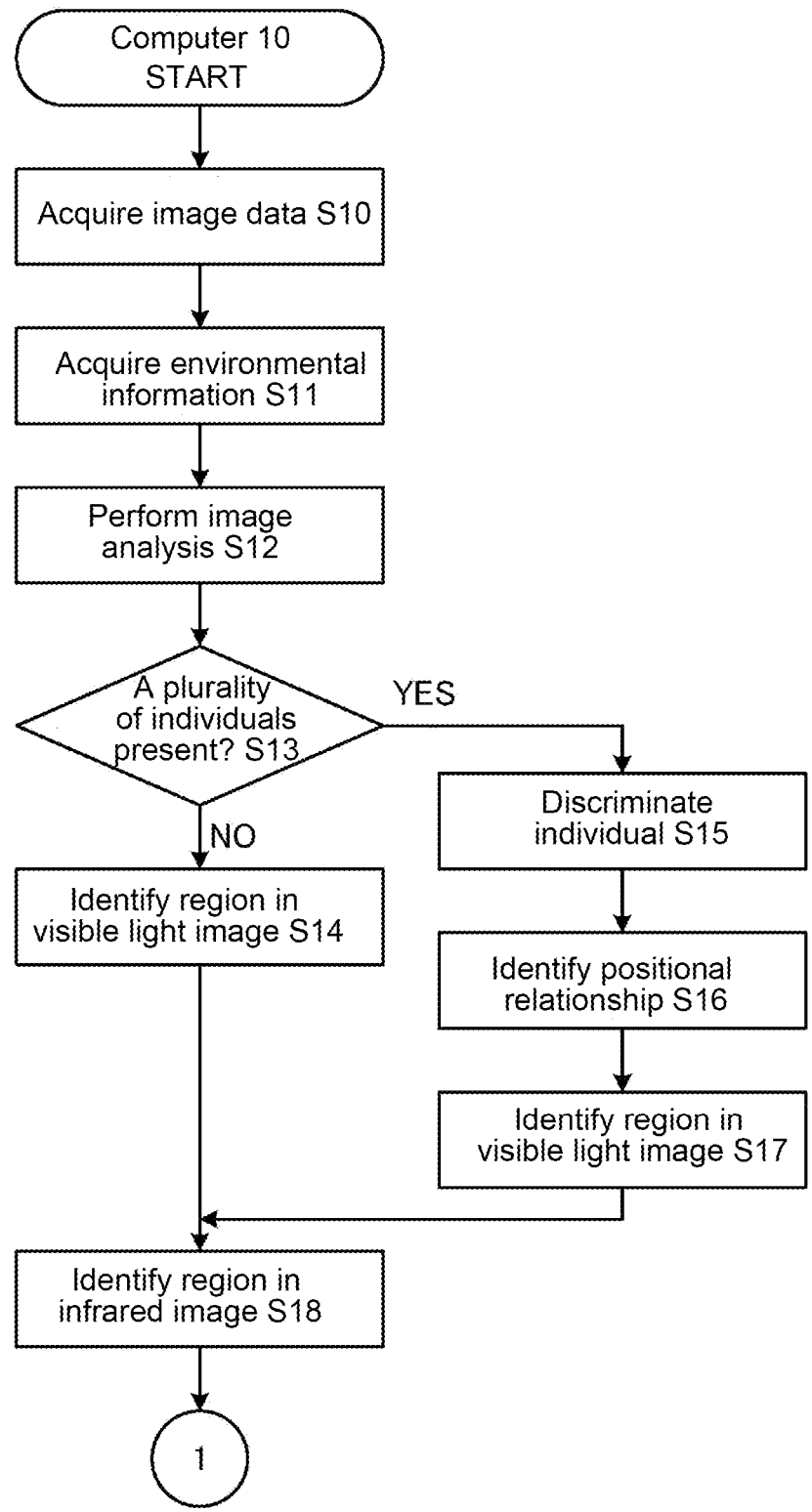
FIG. 4 is a flowchart illustrating a plant diagnosis process executed by the computer 10.
Figure 5:
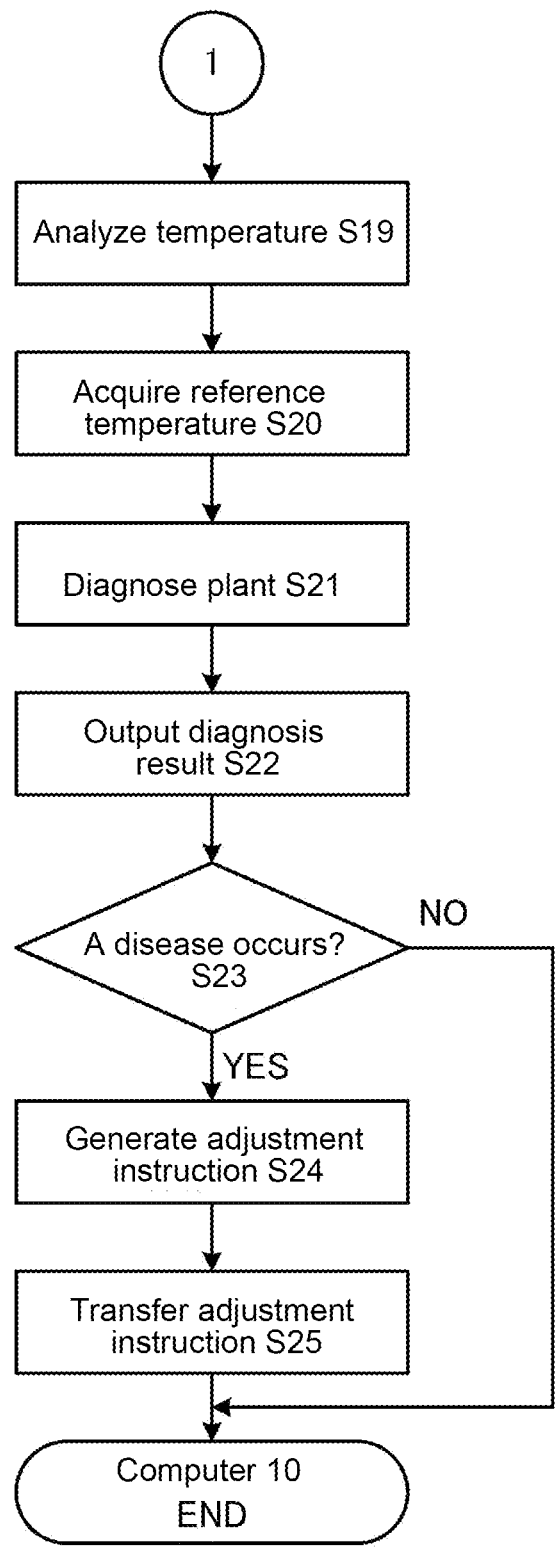
FIG. 5 is a flowchart illustrating the plant diagnosis process executed by the computer 10.

Based on FIG. 4 and FIG. 5, a plant diagnosis process executed by the plant diagnosis system 1 will be described. FIG. 4 and FIG. 5 are flowcharts illustrating the plant diagnosis process executed by the computer 10. The process executed by each module described above will be described together with this processing.

First, the image data acquisition module 20 acquires image data of the visible light image and the infrared image of the plant (step S10). In step S10, the image data acquisition module 20 acquires visible light image data that is the visible light image imaged by the visible light camera and infrared image data that is the infrared image imaged by the infrared camera. The image data acquisition module 20 acquires the visible light image data and the infrared image data at a plurality of time points such as at predetermined time intervals or at preset times. The visible light image data and the infrared image data acquired by the image data acquisition module 20 are imaged from the same imaging point and are data of the same target. Note that, in the following description, it is assumed that the computer 10 executes the plant diagnosis based on the visible light image data and the infrared image data at a predetermined time point.

Figure 6:
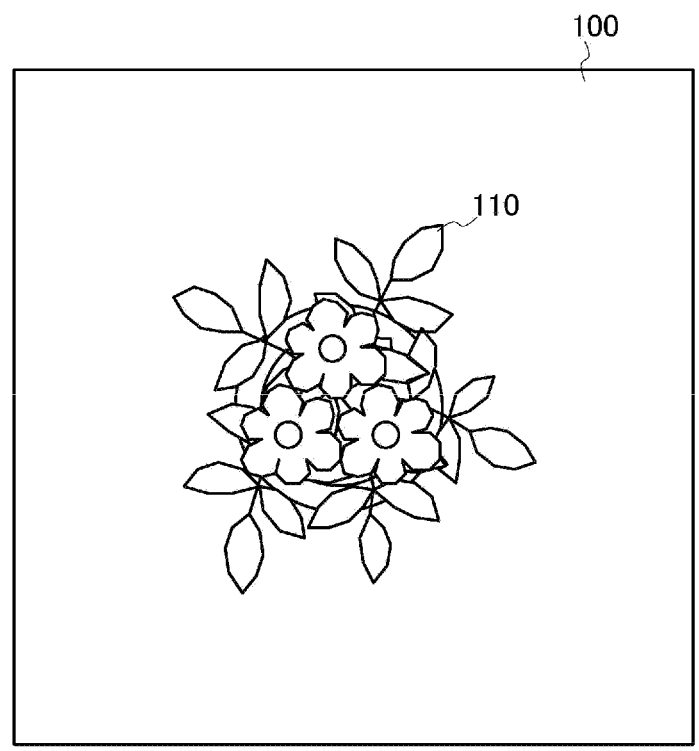
FIG. 6 is a diagram schematically illustrating an example of visible light image data acquired by the computer 10.

Based on FIG. 6, the visible light image data of the plant acquired by the image data acquisition module 20 will be described. FIG. 6 is a diagram schematically illustrating an example of the visible light image data acquired by the image data acquisition module 20. The image data acquisition module 20 acquires a visible light image 100 indicating the visible light image data. In the visible light image 100, a plant 110 is reflected. Further, landscape, natural object, artificial object, and the like other than the plant 110 may be reflected in the visible light image 100, but are omitted for simplification of the description. Further, a plurality of the plants 110 or plant different from the plant 110 may be reflected in the visible light image 100.

Figure 7:
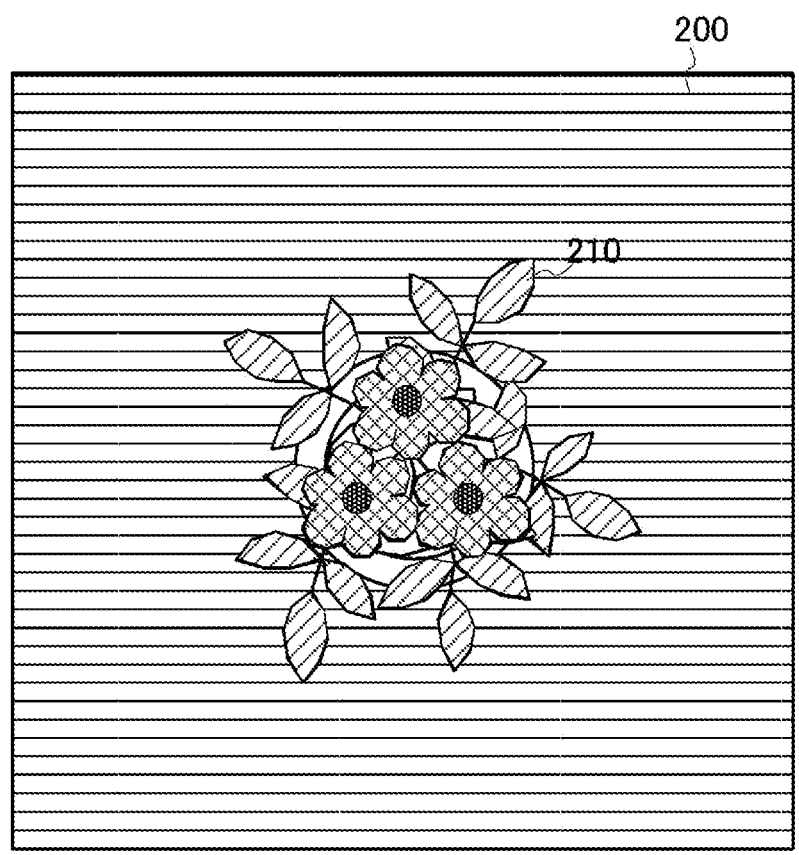
FIG. 7 is a diagram schematically illustrating an example of infrared image data acquired by the computer 10.

Based on FIG. 7, the infrared image data of the plant acquired by the image data acquisition module 20 will be described. FIG. 7 is a diagram schematically illustrating an example of the infrared image data acquired by the image data acquisition module 20. The image data acquisition module 20 acquires an infrared image 200 indicating the infrared image data. In the infrared image 200, a plant 210 is reflected. Further, landscape, natural object, artificial object, and the like other than the plant 210, may be reflected in the infrared image 200, but are omitted for simplification of the description. In the infrared image 200, each temperature is indicated by hatching for convenience. Further, a plurality of the plants 210 or plant different from the plant 210 may be reflected in the infrared image 200.

The environmental information acquisition module 21 acquires environmental information indicating the living environment of the plant (step S11). In step S11, the environmental information acquisition module 21 acquires, as environmental information, brightness, wind direction, wind speed, temperature, ambient temperature, humidity, atmospheric pressure and the like. The environmental information acquisition module 21 acquires the environmental information from various sensors (not shown) such as a brightness sensor, a wind direction and wind speed sensor, a temperature sensor, a humidity sensor, and a pressure sensor. The environmental information acquisition module 21 acquires the environmental information at the same time as the visible light image data and the infrared image data being acquired. These various sensors are disposed adjacent the plant or adjacent a place where the plant is planted.

Note that, various sensors may be sensors detecting environmental information other than the example described above. Further, the disposed position of various sensors can be appropriately changed into a position where the living environment of the plant not only the example described above can be detected. Further, the process of step S11 may be omitted. In this case, after the process of step S10 described above is executed, the process of step S12 described later may be executed.

The visible light image analysis module 40 performs image analysis for the acquired visible light image data (step S12). In step S12, the visible light image analysis module 40 extracts the feature value and the color of the visible light image data, and discriminates the plant presents in the visible light image data. In step S12, for example, the visible light image analysis module 40 compares the feature value extracted from the visible light image data with the feature value of the plant stored in advance in the storage module 30, extracts the plant having coincident feature, and discriminates that the extracted plant presents in the visible light image data. Further, for example, the visible light image analysis module 40 compares RGB values extracted from the visible light image data with RGB values of the plant stored in advance in the storage module 30, extracts the plant having coincident or similar RGB values, and discriminates that the extracted plant presents in the visible light image data.

The visible light image analysis module 40 determines whether a plurality of individuals present in the visible light image data as the result of the image analysis (step S13). In step S13, the visible light image analysis module 40 determines whether a plurality of individuals present by determining whether a plurality of plants present in the visible light image data. The visible light image analysis module 40 determines whether a plurality of individuals of one species of plants is present, or individuals of a plurality of species of plants are present, and the like.

In step S13, when the visible light image analysis module 40 determines that a plurality of individuals do not present (step S13 NO), that is, when it is determined that only one individual presents in the visible light image data, the visible light image analysis module 40 identifies regions corresponding to a plurality of predetermined sites of one individual (step S14). In step S14, the predetermined site is, for example, a part of the structure such as a flower, a branch, a leaf, or a preset site. The visible light image analysis module 40 identifies, for example, a region corresponding to a flower, a branch, or a leaf. The visible light image analysis module 40 extracts a flower, a branch, or a leaf present in the visible light image data from the feature value, and identifies the extracted position as the region corresponding to the predetermined site. At this time, the visible light image analysis module 40 identifies a plurality of regions corresponding to the plurality of predetermined sites respectively. Further, the visible light image analysis module 40 extracts a flower, a branch, or a leaf present in the visible light image data from the RGB values, and identifies the extracted position as the region corresponding to the predetermined site.

Figure 8:
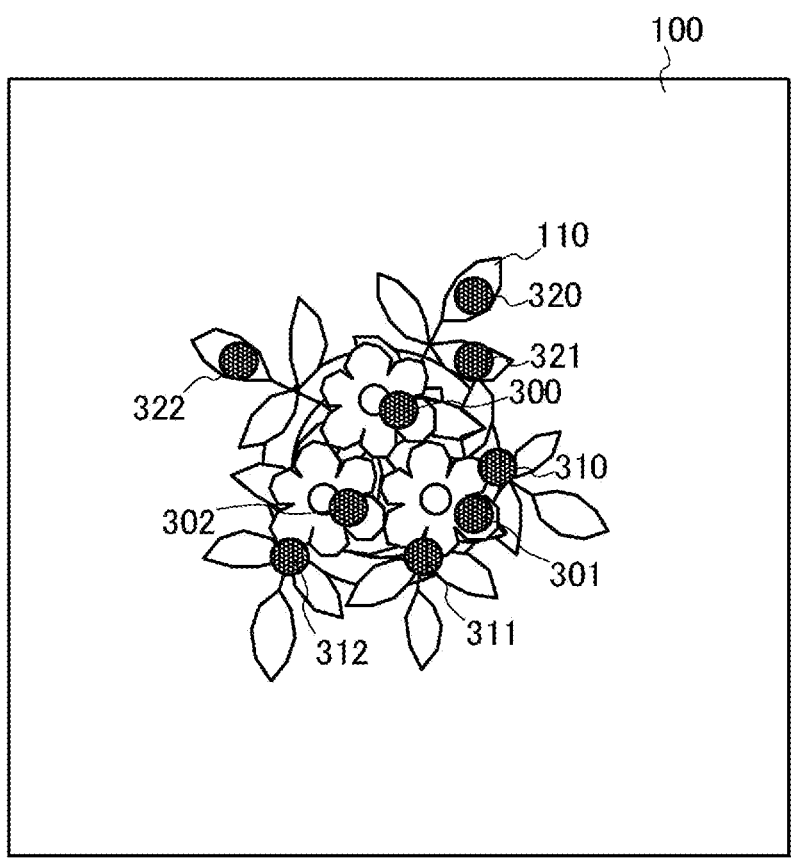
FIG. 8 is a diagram schematically illustrating an example of a state in which the computer 10 identifies a predetermined site in a visible light image.

Based on FIG. 8, the region corresponding to the predetermined site that the visible light image analysis module 40 identifies will be described. FIG. 8 is a diagram schematically illustrating an example of a state in which the visible light image analysis module 40 identifies a predetermined site. In FIG. 8, the visible light image analysis module 40 identifies, based on the feature value and the color, regions in the visible light image 100 in which the predetermined sites such as flowers, branches, or leaves are located. That is, the visible light image analysis module 40 identifies the regions corresponding to sites of flowers 300 to 302, branches 310 to 312, and leaves 320 to 322 of the plant 110. In FIG. 8, the identified regions are indicated by hatching for convenience. Although the region refers to a part of each site, it may refer to the entire corresponding site. Note that, the number, types and positions of the sites to be identified can be changed appropriately.

On the other hand, in step S13, when the visible light image analysis module 40 determines that a plurality of individuals present (step S13 YES), that is, when it determines the plurality of individuals such as a first individual, a second individual, and a third individual present in the visible light image data, the visible light image analysis module 40 respectively identifies the plurality of individuals (step S15). Note that, in the following description, it is assumed that the visible light image data includes a first individual and a second individual.

The visible light image analysis module 40 identifies the positional relationship of each of the plurality of individuals (step S16). In step S16, the visible light image analysis module 40 identifies the positional relationship between the first individual and the second individual based on positions in the visible light image. The visible light image analysis module 40 identifies the relative position or the absolute position of the first individual and the second individual. The positional relationship is, for example, which one is closer to the imaging point, coordinates in the visible light image, and the like. Note that, the process of step S16 is not limited to the positional relationship between the first individual and the second individual, and may be the positional relationship with another individual.

The visible light image analysis module 40 identifies a region corresponding to the predetermined site for each of a plurality of individuals (step S17). In the process of step S17, the process of step S14 described above is executed with respect to each plant that presents in the visible light image data.

The infrared image analysis module 41 identifies a region in the infrared image corresponding to the identified region in the visible light image (step S18). In step S18, the infrared image analysis module 41 identifies the region of the infrared image data corresponding to the identified region of the site of the plant by comparing the visible light image data with the infrared image data. The infrared image analysis module 41 acquires the position of the region in the visible light image as coordinates, and identifies a position coincident with the acquired coordinates as the region in the infrared image corresponding to the identified region in the visible light image.

Figure 9:
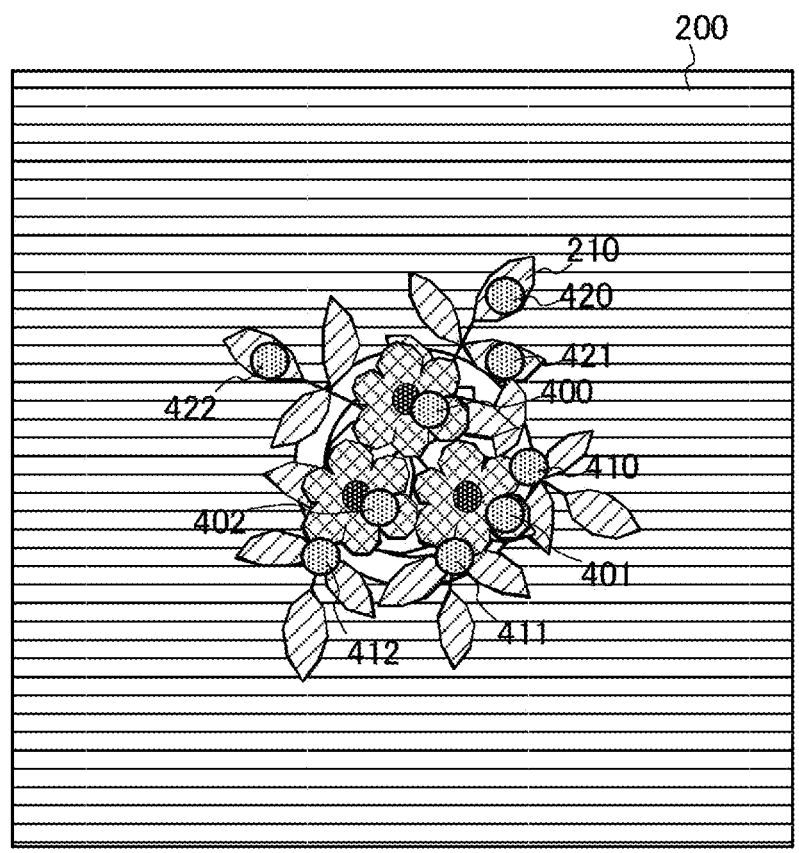
FIG. 9 is a diagram schematically illustrating an example of a state in which the computer 10 identifies a region in an infrared image.

Based on FIG. 9, the region in the infrared image corresponding to the region in the visible light image that the infrared image analysis module 41 identifies will be described. FIG. 9 is a diagram schematically illustrating an example of a state in which the infrared image analysis module 41 identifies the region in the infrared image. In FIG. 9, regions in the infrared image 200 corresponding to the sites of the flowers 300 to 302, the branches 310 to 312, and the leaves 320 to 322 of the identified plant 110 in the visible light image 100 described above is identified. It is identified by comparing the position in the visible light image 100 with the position in the infrared image 200. The infrared image analysis module 41 acquires the position coordinates of each site in the visible light image 100, and identifies the position in the infrared image corresponding to the acquired position coordinates as the region in the infrared image corresponding to the region in the visible light image. The infrared image analysis module 41 identifies sites of flowers 400 to 402, branches 410 to 412, and leaves 420 to 422 of the plant 210. In FIG. 9, the identified regions are indicated by hatching for convenience. The region refers to a part or the entire site depending on the identified site in the visible light image described above. Note that, the number and positions of the sites can be appropriately changed according to the visible light image.

The temperature analysis module 42 analyzes the temperature of the identified region in the infrared image data (step S19). In step S19, the temperature analysis module 42 acquires the temperature of each region based on the infrared image data.

The temperature analysis module 42 acquires a plurality of reference temperatures corresponding to each of the plurality of sites of the plant from a reference temperature database stored in the storage module 30 (step S20). The storage module 30 stores the plurality of reference temperatures corresponding to each site in advance, and in step S20, the temperature analysis module 42 acquires the stored reference temperatures. At this time, the reference temperature of the site corresponding to the identified region in the infrared image data is acquired.

Reference Temperature Database

Based on FIG. 10, the reference temperature database stored in the storage module 30 will be described. FIG. 10 is a diagram illustrating an example of the reference temperature database stored in the storage module 30. In FIG. 10, the storage module 30 associates the name of a site and the reference temperature of this site, and stores them. That is, the storage module 30 associates "stem" with "18", associates "branch" with "17", associates "leaf" with "20", and stores them. The storage module 30 stores the reference temperature database for each type of plant. Note that, the storage module 30 may store the reference temperature database not for each type of plant but for each individual plant. In this case, the storage module 30 may acquire the reference temperature for each part of each individual in advance, associate the site and the reference temperature, and store them.

The diagnosis module 43 diagnoses the plant based on the temperature of the identified region in the infrared image (step S21). In step S21, the diagnosis module 43 diagnoses the plant based on any of the acquired temperature, the reference temperature, the temperature of another individual different from one individual, the positional relationship between the first individual and the second individual, the environmental information, or based on any combination of a plurality of these.

A case where the diagnosis module 43 executes the plant diagnosis based on the acquired temperature will be described. The diagnosis module 43 determines whether the temperature of the identified region in the infrared image is an abnormal value, and determines the plant is healthy when it is not an abnormal value. On the other hand, when it is determined that the temperature is an abnormal value, the diagnosis module 43 determines that a disease occurs.

A case where the diagnosis module 43 executes the plant diagnosis based on the reference temperature will be described. The diagnosis module 43 compares the temperature of the identified region in the infrared image with the acquired reference temperature stored in the storage module 30, and calculates the temperature difference between the temperature of the region and the reference temperature. The diagnosis module 43 determines whether the calculated temperature difference is within a predetermined range (for example, within 0.5° C., within 1° C., within 2° C., etc.), and determines the plant is healthy when it is within the predetermined range. On the other hand, when the calculated temperature difference is not within the predetermined range, the diagnosis module 43 determines that a disease occurs.

A case where the diagnosis module 43 executes the plant diagnosis based on temperatures of one individual and another individual different from the one individual will be described. The diagnosis module 43 compares the acquired temperature of the region in the infrared image of the one individual with the temperature of the corresponding region in the infrared image of the other individual different from the one individual, and calculates the temperature difference between the temperatures. The diagnosis module 43 determines whether the calculated temperature difference is within a predetermined range (for example, within 0.5° C., within 1° C., within 2° C., etc.), and determines the plant is healthy when it is within the predetermined range. On the other hand, when the calculated temperature difference is not within the predetermined range, the diagnosis module 43 determines that a disease occurs. Note that, in this case, the diagnosis module 43 may determine whether a disease occurs by comparing the temperature of the one individual or the other individual with the reference temperature described above, and calculating the temperature difference between the one individual and the other individual. That is, the diagnosis module 43 may determine whether a disease occurs in the one individual or the other individual or both based on the reference temperature and the temperature difference.

A case where the diagnosis module 43 executes the plant diagnosis based on the positional relationship between the first individual and the second individual will be described. The diagnosis module 43 compares, among the plurality of individuals that are acquired, the positional relationship between the position of the first individual and the second individual different from the first individual and determines which one is more affected by sunlight, lighting, and the like. It is determined whether the temperature of the first individual or the second individual is higher due to the influence of sunlight, lighting, and the like. The diagnosis module 43 corrects the temperature of the first individual and the second individual by acquiring the environmental information such as ambient temperature, brightness as the influence of the sunlight, lighting, and the like. The diagnosis module 43 compares the corrected temperatures of the first individual and the second individual with the reference temperature described above, and calculates the temperature difference between them. The diagnosis module 43 determines whether the temperature difference is within a predetermined range (for example, within 0.5° C., within 1° C., within 2° C., etc.), and determines the plant is healthy when it is within the predetermined range. On the other hand, when it is determined that the calculated temperature difference is not within the predetermined range, the diagnosis module 43 determines that a disease occurs. Note that, the diagnosis module 43 may determine whether the plant is healthy without using the reference temperature. For example, whether the plant is healthy may be determined based on whether the corrected temperatures of the first individual and the second individual are predetermined temperatures.

A case where the diagnosis module 43 executes the plant diagnosis based on the environmental information acquired from a sensor will be described. The diagnosis module 43 corrects the acquired temperature of the individual based on the environmental information. For example, the diagnosis module 43 acquires humidity, ambient temperature, atmospheric pressure or the like as the environmental information, and corrects the acquired temperature of the individual based on the acquired environmental information. The diagnosis module 43 diagnoses the plant based on the corrected temperature of the individual. Note that, the diagnosis module 43 may determine whether the plant is healthy based on the corrected temperature of the individual and the reference temperature.

The diagnosis module 43 outputs the diagnosis result (step S22). In step S22, the diagnosis module 43 outputs the content of the disease (for example, the name of the disease, a treating method, etc.) as the diagnosis result. When only one individual presents in the visible light image data and the infrared image data, the diagnosis module 43 outputs the diagnosis result of the one individual. Further, when a plurality of individuals present in the visible light image data and the infrared image data, the diagnosis module 43 outputs the diagnosis result for each individual. At this time, the diagnosis module 43 outputs the diagnosis result together with various information that can uniquely identify the individual such as name, identifier, position information of each individual.

Note that, in the above description, the diagnosis module 43 diagnoses the plant based on one visible light image data and one infrared image data, but the plant diagnosis may be performed based on a plurality of visible light image data and infrared image data acquired within a predetermined period. In this case, the plant diagnosis may be performed based on change amount, change width, or the change itself of the temperature of the individual acquired from each infrared image data. Further, the diagnosis module 43 may execute the plant diagnosis based on the average value of the temperatures of individuals acquired from the plurality of infrared image data. For example, the diagnosis module 43 may calculate the temperature difference between the average value of the temperatures and the reference temperature by comparing the average value of the temperatures of the individuals with the reference temperature, and may execute the plant diagnosis based on whether the temperature difference is within a predetermined range.

The diagnosis module 43 determines whether a disease occurs in the individual based on the output diagnosis result (step S23).

In step S23, when the diagnosis module 43 determines that no disease occurs in the individual (step S23 NO), the process ends. Note that, at this time, the diagnosis module 43 may transmit a notification that no disease occurs in the individual to an external terminal device (not illustrated).

In step S23, when the diagnosis module 43 determines that a disease occurs in the individual (step S23 YES), the environment adjustment module 44 generates an adjustment instruction to adjust the living environment based on the information indicating the diagnosis result (step S24). In step S24, the environment adjustment module 44 acquires, based on the content of the diagnosed disease, necessary process based on an adjustment database or the like that associates and stores the disease content and the process. The environment adjustment module 44 generates the adjustment instruction to execute the acquired process. The adjustment instruction includes the necessary process, information such as an identifier and a device ID that can uniquely identifying the environment adjustment device configured to execute the necessary process, and the like.

The adjustment instruction transmission module 22 transmits the adjustment instruction generated by the environment adjustment module 44 in step S24 described above to the environment adjustment device (step S25). The adjustment instruction transmission module 22 transmits the target environment adjustment device based on the information that is included in the adjustment instruction and can uniquely identify the environment adjustment device.

The environmental adjustment device receives the adjustment instruction and executes the necessary process included in the adjustment instruction. For example, the environment adjustment device performs lighting on/off, humidity and temperature control, water sprinkling, drug dispersion, and the like.

The above is the plant diagnosis process.

Note that, in the embodiment described above, the computer 10 executes the process of determining a disease of the plant, in addition to this, the present disclosure is applicable to execute other process of plant diagnosis. For example, the computer 10 may execute a process of determining the need for watering based on the temperature of the plant described above, may execute a process of determining the need for adjusting the brightness based on the temperature and the environmental information of the plant, or may execute other process.

The units and functions described above are realized by the computer (including a CPU, an information processing device, and various terminals) reading and executing a predetermined program. The program is provided, for example, in a form provided from the computer via a network (SaaS: software as a service). Further, the program is provided, for example, in a form of being recorded on a computer-readable recording medium such as a flexible disk, a CD (such as a CD-ROM), and a DVD (such as a DVD-ROM, a DVD-RAM). In this case, the computer reads the program from the recording medium, transfers the program to an internal storage device or an external storage device, stores and executes it. Further, the program may be recorded in advance in a storage device (recording medium) such as a magnetic disk, an optical disk, and a magneto-optical disk, and may be provided from the storage device to the computer via a communication line.

The embodiments of the present disclosure are described above, but the present disclosure is not limited to these embodiments described above. Further, the effects described in the embodiments of the present disclosure are merely examples of the most suitable effects resulting from the present disclosure, and the effects of the present disclosure are not limited to the effects described in the embodiments of the present disclosure.

REFERENCE SIGNS LIST

1 Plant diagnosis system; 10 Computer

What is claimed is:

1. A computer system comprising: a processor and a storage; wherein the storage stores a processor-executable program executed by the processor, and the program comprises:
   a storage unit configured to store a feature value or an RGB value of a plant in advance;
   a first acquisition unit configured to acquire a visible light image and an infrared image that are imaged by a camera;
   a first image processing unit configured to compare a feature value or an RGB value, which is extracted from data of the visible light image, with the feature value or the RGB value of the plant stored in the storage unit, discriminate a plant present in the data of the visible light image, and identify a region, which corresponds to a predetermined site of the discriminated plant, according to the feature value or the RGB value;
   a second image processing unit configured to identify a region, in the infrared image, which corresponds to the identified region in the visible light image; and
   a diagnosis unit configured to diagnosis the plant based on a temperature of the identified region in the infrared image, wherein the diagnosis unit uses the temperature of another individual plant when diagnosing one of a plurality of individual plants, wherein the another individual plant is different from the one of the plurality of individual plants.

2. The computer system according to claim 1, wherein the program further comprises:
   a storage unit configured to store a plurality of reference temperatures corresponding to each of a plurality of sites of the plant, wherein
   the first image processing unit identifies a plurality of regions corresponding to each of a plurality of predetermined sites, and
   the diagnosis unit compares temperatures in the plurality of regions identified by the second image processing unit with each of the reference temperatures.

3. The computer system according to claim 1, wherein the first image processing unit respectively discriminates a plurality of individual plants imaged by the camera, and the diagnosis unit outputs a diagnosis result for each of the plurality of individual plants.

4. The computer system according to claim 3, wherein the first image processing unit identifies a positional relationship between a first individual plant and a second individual plant comprised in the plurality of individual plants for determining an affection of sunlight and lighting, and
   the diagnosis unit uses the positional relationship.

5. The computer system according to claim 1, wherein the program further comprises:
   a second acquisition unit configured to acquire environmental information indicating a living environment of the plant, wherein
   the diagnosis unit uses the environmental information.

6. The computer system according to claim 1, wherein
   the first acquisition unit acquires the visible light image and the infrared image at a plurality of time points respectively, and
   the diagnosis unit uses a plurality of the visible light images and a plurality of the infrared images acquired within a predetermined period.

7. The computer system according to claim 1, wherein the program further comprises:
   an adjustment unit configured to adjust a living environment based on information indicating the diagnosis result output by the diagnosis unit.

8. A plant diagnosis method, comprising:
   storing a feature value or an RGB value of a plant in a storage unit in advance;
   acquiring a visible light image and an infrared image that are imaged by a camera;
   comparing a feature value or an RGB value, which is extracted from data of the visible light image, with the feature value or the RGB value of the plant stored in the storage unit,
   discriminating a plant present in the data of the visible light image, and identifying a region, which corresponds to a predetermined site of the discriminated plant, according to the feature value or the RGB value;
   identifying a region, in the infrared image, which corresponds to the identified region in the visible light image; and
   diagnosing the plant based on a temperature of the identified region in the infrared image, using the temperature of another individual plant when diagnosing one of a plurality of individual plants, wherein the another individual plant is different from the one of the plurality of individual plants.

9. A non-transitory computer-readable medium causing a computer system to execute:
   storing a feature value or an RGB value of a plant in a storage unit in advance;
   acquiring a visible light image and an infrared image that are imaged by a camera;
   comparing a feature value or an RGB value, which is extracted from data of the visible light image, with the feature value or the RGB value of the plant stored in the storage unit, discriminating a plant present in the data of the visible light image, and identifying a region, which corresponds to a predetermined site of the discriminated plant, according to the feature value or the RGB value; and
   identifying a region, in the infrared image, which corresponds to the identified region in the visible light image;

diagnosing the plant based on a temperature of the identified region in the infrared image, using the temperature of another individual plant when diagnosing one of a plurality of individual plants, wherein the another individual plant is different from the one of the plurality of individual plants.

\* \* \* \* \*